United States Patent [19]
Arcuri et al.

[11] Patent Number: 5,998,676
[45] Date of Patent: Dec. 7, 1999

[54] CONVERSION OF PICRATE TO PICRIC ACID IN A LIQUID-LIQUID TWO PHASE SYSTEM

[75] Inventors: Kym B. Arcuri, Greenwell Springs, La.; Dwayne A. Goetsch, Excelsior, Minn.

[73] Assignee: Gradient Technology, Excelsior, Minn.

[21] Appl. No.: 09/149,938

[22] Filed: Sep. 9, 1998

Related U.S. Application Data

[60] Provisional application No. 60/058,292, Sep. 9, 1997.

[51] Int. Cl.$^6$ .................................................... C07C 205/00
[52] U.S. Cl. ........................................... 568/710; 568/708
[58] Field of Search ...................................... 568/708, 710

[56] References Cited

U.S. PATENT DOCUMENTS

| 4,804,480 | 2/1989 | Jayawant | 210/759 |
| 5,530,175 | 6/1996 | Johnson et al. | 588/203 |

*Primary Examiner*—Michael L. Shippen
*Attorney, Agent, or Firm*—Henry E. Naylor

[57] ABSTRACT

A process for the conversion of a picrate salt, preferably ammonium pricrate, to picric acid by acidifying the picrate salt in a two phase liquid system. One phase is an aqueous phase which contains an acid which is effective for acidifying ammonium picrate to picric acid and the other phase is an organic solvent phase in which the picric acid is soluble.

16 Claims, No Drawings

5,998,676

CONVERSION OF PICRATE TO PICRIC ACID IN A LIQUID-LIQUID TWO PHASE SYSTEM

This application claims priority of Provisional Application 60/058,292 filed Sep. 9, 1997.

FIELD OF THE INVENTION

The present invention relates to a process for the conversion of a picrate salt, preferably ammonium pricrate, to picric acid by acidifying the picrate salt in a two phase liquid system. One phase is an aqueous phase which contains an acid which is effective for acidifying ammonium picrate to picric acid and the other phase is an organic solvent phase in which the picric acid is soluble.

BACKGROUND OF THE INVENTION

There is a need to destroy, or reclaim, explosive materials as part of the demilitarization effort. Procedures conventionally used to demilitarize conventional munitions include incineration of reclaimed explosives and open burning or detonation. Some explosive materials, such as ammonium picrate, also known as Explosive "D", are of high enough purity to be economically suitable for conversion to higher value chemicals.

The destruction of nitrogen-containing explosives has been the subject of various disclosures. For example, German patent publication DE 413 147-A1 discloses the hydrogenation of nitro-aromatic explosives in the presence of an alcohol solvent, hydrogen, and a catalyst at a temperature of about 40° C. to 100° C. Also, U.S. Pat. No. 4,661,179 discloses a process for destroying waste explosives containing nitro, nitrate, or nitroamino groups by hydrogenation. Further, U.S. Pat. No. 5,582,119 teaches a method for destroying explosive waste, such as those containing ammonium picrate, by use of a vessel containing a hot granular bed of sand to ignite the waste and to dampen explosive forces generated by its ignition.

U.S. Pat. No. 5,530,175 discloses a process for converting ammonium picrate to oxygenated products, particularly hydroquinone or cyclohexanediol and ammonia, by hydrogenation over a supported Group VIII metal catalyst. The ammonium picrate is dissolved in a suitable solvent, then hydrogenated at a temperature of about 25° to 250° C., followed by separation of the resulting products and ammonia.

It is also known in the art that ammonium picrate can be converted to picric acid by acidification with a strong acid, at an appropriate pH and acid/salt ratio in an aqueous system. The concentration of picric acid must be kept relatively low because as the concentration of picric acid increases, its rate of formation decreases.

While there exists methods for converting ammonium picrate to more useful products, such as to picric acid, there remains a need for processes that can do this conversion more efficiently and economically.

SUMMARY OF THE INVENTION

In accordance with the present invention there is provided a process for converting a picrate salt, preferably ammonium picrate to picric acid which process comprises reacting said picrate salt with an aqueous solution of a strong acid which is effective for converting said picrate salt to picric acid, said reaction talking place in the presence of an organic solvent phase in which the picric acid is substantially soluble, and into which the picric acid dissolves upon formation.

In a preferred embodiment of the present invention the solvent is selected from the group consisting of xylene, toluene, and mixtures thereof.

In another preferred embodiment of the present invention the acid is a mineral acid selected from the group consisting of sulfuric acid, nitric acid, and chloric acid.

In still another preferred embodiment of the present invention the conversion of picrate to picric acid is performed at a pH between about 3 and 5.

DETAILED DESCRIPTION OF THE INVENTION

The acidification of ammonium picrate to picric aid is known in the art and is generally preformed in an aqueous medium wherein ammonium picrate is reacted with a suitable acid, typically a strong acid such as a mineral acid, at an effective pH and within a suitable acid/salt ratio. As the reaction proceeds, the concentration of picric acid in the aqueous phase increases to a level that will significantly slow the acidification reaction, thus severely affecting the economics of the process. Consequently, it is necessary to maintain a relatively low concentration of picric acid in the aqueous phase in order to maintain acceptable acidification reaction rates. This is not generally acceptable because maintaining a low concentration of picric acid results in a substantially less efficient process. Thus, it would be highly desirable to be able to produce picric acid from ammonium picrate so that the picric acid produced would not adversely effect the rate of picric acid formation.

The process of the present invention solves the above problem by providing a two phase system. Both phases are liquid, wherein one phase is an aqueous phase in which the acidification reaction takes place, and the other is an organic phase in which the picric acid is soluble. Thus, the acidification reaction is not adversely affected because as the picric acid is formed it dissolves into the organic phase, thereby keeping the concentration of picric acid in the aqueous phase relatively low. As previously mentioned the organic phase is comprised of an organic solvent in which picric acid is substantially soluble. Organic solvents which are suitable for use in the present invention are those which have a relatively low vapor pressure (boiling point), and in which the picric acid will readily dissolve, and which have substantially negligible aqueous solubility. In other words, the organic solvent is one which has a relatively low partition coefficient with respect to the aqueous phase but in which the picrate acid has a relatively high partition coefficient. That is, the picric acid will strongly favor the organic phase over the aqueous phase. Preferred solvents include toluene and xylene, as well as other suitable organic materials which can be used. Further, the use of an organic solvent increases the efficiency of the acidification process since a smaller acid-ammonium picrate contact volume for producing a given amount of picric acid. The solubility of picric acid in many commercially available organic solvents (i.e. toluene) is 5 to 25 times higher than its solubility in water. The use of an organic solvent with a low aqueous solubility and high vapor pressure simplifies the picric acid recovery step. The insoluble organic phase containing the picric acid product is separated from the aqueous phase using conventional state of the art oil-water separation technology.

Acids suitable for use in the practice of the present invention are those acids which are strong enough to effectively acidify ammonium picrate to picric acid in an aqueous medium. A strong acid is needed in order to provide the hydronium ions necessary to produce picric acid. The specific acid and concentration level depends upon several technical issues which ultimately affect process economics. The amount of acid used will depend upon such things as the equilibrium of the acidification as well as the impact on the solubility of the resulting acid and salts. Non-limiting examples of such acids are the mineral acids selected from the group consisting of sulfuric acid, nitric acid, and chloric acid. A preferred acid would be one which results in an ammonium salt product that has commercial value. Thus, the most preferred acid, from a commercial point of view is nitric acid because the resulting ammonium nitrate could be used for agricultural purposes.

The instant process can be practiced in any suitable manner as long as the two liquid phases are present during the formation of picric acid and before the concentration of picric acid reaches unacceptable high levels in the aqueous phase. For example, the strong acid can be added to an aqueous solution of ammonium picrate, thereby resulting in an acidification reaction wherein picric acid is producted, as well as an ammonium salt. The amount of acid used will depend on such things as the level of pH needed to ensuer relatively high picrate acidification. Typically the pH will be less than about 5, such as between about 3 and 5, although a lower pH may also be used. The organic solvent is then added before the concentration of picric acid increases to a level that would significantly decrease the rate of acidification. The concentration of ammonium picrate in water can vary depending on such things as the desired quality of the product picric acid. It is preferred that less than about 20 wt. %, more preferably less than about 15 wt. % of ammonium picrate be present, based on the total weight of ammonium picrate and water. Of course, the temperature of the aqueous solution will play a role in the potential concentration of ammonium picrate. For example, the solubility of ammonium picrate will increase with increasing temperatures. The organic phase, containing the picric acid, can be drawn off and the picric acid separated from the organic solvent by conventional separation techniques, such as by flashing the solvent and recovering the remaining picric acid. The organic solvent can then be recycled.

As the reaction proceeds, the concentration of salt in the aqueous phase will increase to unacceptable levels. When this happens, a fraction of the salt-containing aqueous solution can be withdrawn and the salt recovered by conventional techniques, such as in a crystallizer vessel. This will help ensure that the level of salt be maintained at level that will not adverely effect the acidification reaction.

Another process scheme can be envisioned wherein a mixture of water and organic solvent are provided into which is added ammonium picrate and a strong acid. The mixture is then throughly stirred and the organic phase containing the picric acid drawn off and passed to a separation step where the picric acid is separated from the solvent by conventional means. The organic solvent can be recycled.

A solvent wash may be employed with any of the process options to achieve a higher product purity and avoid the use of excess acid or water. The limited solubility available thus far indicates that picric acid has a relatively high solubility in ethyl alcohol compared to ammonium picrate (7.5 versus 0.35 gms/100 gms water when no acid is present). Consequently, an alcohol wash may be effective in removing trace acid, water, and/or dissolved ammonium salt.

What is claimed is:

1. A process for converting a picrate salt to picric acid which process comprises reacting said picrate salt with an aqueous solution of a strong acid which is effective for converting said picrate salt to picric acid, said reaction taking place in the presence of an organic solvent phase in which the picric acid is substantially soluble, and into which the picric acid dissolves upon formation.

2. The process of claim 1 wherein the solvent is selected from the group consisting of xylene, toluene, and mixtures thereof.

3. The process of claim 1 wherein the acid is a mineral acid.

4. The process of claim 3 wherein the mineral acid is selected from the group consisting of sulfuric acid, nitric acid, and chloric acid.

5. The process of claim 4 wherein the acid is nitric acid.

6. The process of claim 1 wherein the conversion of picrate to picric acid is performed at a pH less than about 5.

7. The process of claim 6 wherein the conversion of picrate to picric acid is performed at a pH between about 3 and 5.

8. The process of claim 1 wherein the organic solvent containing dissolved picric acid is separated from the aqueous solution.

9. The process of claim 8 wherein the picric acid is separated from the organic solvent.

10. The process of claim 9 wherein the organic solvent is recycled.

11. A process for converting ammonium picrate salt to picric acid which process comprises reacting said ammonium picrate with an aqueous solution of a strong acid selected from the group consisting of sulfuric acid, nitric acid, and chloric acid, said reaction taking place in the presence of an organic solvent phase in which the picric acid is substantially soluble, and into which the picric acid dissolves upon formation.

12. The process of claim 11 wherein the ammonium picrate is converted to picric acid at a pH between about 3 and 5.

13. The process of claim 11 wherein the solvent is selected from the group consisting of xylene, toluene, and mixtures thereof.

14. The process of claim 11 wherein the organic solvent containing dissolved picric acid is separated from the aqueous solution.

15. The process of claim 14 wherein the picric acid is separated from the organic solvent.

16. The process of claim 15 wherein the organic solvent is recycled.

* * * * *